(12) United States Patent
Zhang

(10) Patent No.: US 11,412,981 B2
(45) Date of Patent: Aug. 16, 2022

(54) INTELLIGENT DEVICE WEARING DETECTION METHOD AND INTELLIGENT DEVICE

(71) Applicant: Honor Device Co., Ltd., Shenzhen (CN)

(72) Inventor: Hong Zhang, Shenzhen (CN)

(73) Assignee: Honor Device Co., Ltd., Shenzhen (CN)

( * ) Notice: Subject to any disclaimer, the term of this patent is extended or adjusted under 35 U.S.C. 154(b) by 820 days.

(21) Appl. No.: 16/334,510

(22) PCT Filed: Sep. 20, 2016

(86) PCT No.: PCT/CN2016/099417
§ 371 (c)(1),
(2) Date: Mar. 19, 2019

(87) PCT Pub. No.: WO2018/053677
PCT Pub. Date: Mar. 29, 2018

(65) Prior Publication Data
US 2019/0388027 A1    Dec. 26, 2019

(51) Int. Cl.
*G16H 40/67* (2018.01)
*A61B 5/00* (2006.01)
(Continued)

(52) U.S. Cl.
CPC ............ *A61B 5/681* (2013.01); *A61B 5/0011* (2013.01); *A61B 5/02055* (2013.01);
(Continued)

(58) Field of Classification Search
CPC ... A61B 5/681; A61B 5/0011; A61B 5/02055; A61B 5/02433; A61B 5/02444;
(Continued)

(56) References Cited

U.S. PATENT DOCUMENTS

| 2015/0289802 | A1* | 10/2015 | Thomas | G01P 15/02 |
| | | | | 600/301 |
| 2016/0249864 | A1* | 9/2016 | Kang | A61B 5/7285 |
| | | | | 340/870.07 |

(Continued)

FOREIGN PATENT DOCUMENTS

| CN | 104510467 A | 4/2015 |
| CN | 104516479 A | 4/2015 |

(Continued)

*Primary Examiner* — An T Nguyen
(74) *Attorney, Agent, or Firm* — Slater Matsil, LLP

(57) ABSTRACT

An intelligent device and wearing method. The method includes, for an intelligent device having a first sensor and a second sensor, obtaining a measurement value of the first sensor, when the measurement value of the first sensor is greater than a first threshold, determining that the intelligent device is in a worn state, when the measurement value of the first sensor is less than a second threshold, determining that the intelligent device is in a not-worn state, where the first threshold is greater than the second threshold, when the measurement value of the first sensor is between the first threshold and second threshold, turning on the second sensor, turning on the second sensor, obtaining a measurement value of the second sensor, and determining, according to the measurement value of the second sensor, that the intelligent device is in the worn state or in the not-worn state.

20 Claims, 11 Drawing Sheets

(51) Int. Cl.
*A61B 5/0205* (2006.01)
*A61B 5/024* (2006.01)
*G06F 1/3231* (2019.01)
*G06F 1/32* (2019.01)
*G06F 1/3206* (2019.01)
*G06F 1/16* (2006.01)
*G08B 21/04* (2006.01)

(52) U.S. Cl.
CPC ...... *A61B 5/02433* (2013.01); *A61B 5/02444* (2013.01); *A61B 5/6844* (2013.01); *G06F 1/163* (2013.01); *G06F 1/32* (2013.01); *G06F 1/3206* (2013.01); *G06F 1/3231* (2013.01); *G08B 21/0446* (2013.01); *G08B 21/0453* (2013.01); *A61B 2560/0209* (2013.01); *A61B 2560/029* (2013.01); *A61B 2562/0219* (2013.01); *A61B 2562/0257* (2013.01); *Y02D 10/00* (2018.01)

(58) Field of Classification Search
CPC .......... A61B 5/6844; A61B 2560/0209; A61B 2560/029; A61B 2562/0219; A61B 2562/0257; G06F 1/163; G06F 1/32; G06F 1/3206; G06F 1/3231; G08B 21/0446; G08B 21/0453; Y02D 10/00
See application file for complete search history.

(56) References Cited

U.S. PATENT DOCUMENTS

| | | | |
|---|---|---|---|
| 2017/0045928 A1* | 2/2017 | Ishikawa | G06F 1/3218 |
| 2019/0015045 A1 | 1/2019 | Li | |
| 2019/0086239 A1* | 3/2019 | Kreisfeld | G01N 27/83 |
| 2019/0388027 A1* | 12/2019 | Zhang | G06F 1/32 |
| 2020/0367827 A1* | 11/2020 | Min | A61B 5/681 |
| 2020/0374617 A1* | 11/2020 | Liu | H04R 1/1016 |
| 2021/0014603 A1* | 1/2021 | Wei | H04R 5/04 |
| 2021/0118564 A1* | 4/2021 | Liu | G16H 40/63 |

FOREIGN PATENT DOCUMENTS

| | | |
|---|---|---|
| CN | 105139596 A | 12/2015 |
| CN | 105758452 A | 7/2016 |
| EP | 2211319 A1 | 7/2010 |
| WO | 2015079436 A1 | 6/2015 |

* cited by examiner

INTELLIGENT DEVICE WEARING DETECTION METHOD AND INTELLIGENT DEVICE

CROSS-REFERENCE TO RELATED APPLICATIONS

This application is a national stage of International Application No. PCT/CN2016/099417, filed on Sep. 20, 2016. The aforementioned application is hereby incorporated by reference in its entirety.

TECHNICAL FIELD

Embodiments of the present invention relate to the terminal field, and in particular, to an intelligent device wearing detection method and an intelligent device.

BACKGROUND

Currently, there are various wearable intelligent devices, which are also referred to as intelligent wearable devices. A wearing detection solution allows to detect whether a user wears an intelligent wearable device, that is, detect that the intelligent device is in a worn state and/or in a not-worn state. The intelligent device supports different functions based on different statuses of the intelligent device. This policy has been widely applied to the intelligent wearable devices. For example, after a locking password is set for an Apple® watch, a device locking state is correlated with a wearing status. When a device is not worn, an unlocking password needs to be entered each time the device is used. However, after the device is worn, the unlocking password needs to be entered only for the first use. Fitbit® surge determines, based on whether the device is worn, whether to start heart rate measurement. Heart rate measurement is not started when the user does not wear the device.

In the prior art, a wearing detection method for these devices uses a single infrared (IR) sensor and/or an acceleration sensor (A-Sensor) for detection. For example, when an Apple watch uses a single IR sensor for wearing detection and a screen is on, wearing status detection is started. If a worn state is detected, and no password has been entered for wearing this time, a password needs to be entered. After the screen is off in the worn state, non-wearing status detection is continuously being performed. If the device is in a not-worn state and the screen is off, wearing status detection is not performed. Fitbit surge uses an acceleration sensor for wearing detection. When the device is statically placed on a desktop, the acceleration sensor cannot detect any action, and photoplethysmogram (PPG) measurement immediately stops. When the device is wobbling, the acceleration sensor detects the action, and PPG measurement immediately starts.

It can be learned from the foregoing that in the prior art, the Apple watch uses the IR sensor for wearing detection, and IR measurement consumes relatively high power. Fitbit surge determines a wearing status based on the acceleration sensor. When the device is placed on the desktop and the device is slightly wobbled by a hand, the device is then considered entering a worn state and PPG measurement starts, leading to low accuracy. That is, in the prior-art wearing detection method, it is difficult to reduce power consumption while ensuring detection accuracy.

SUMMARY

Embodiments of the present invention provide an intelligent device wearing detection method and an intelligent device, so as to reduce power consumption while ensuring detection accuracy.

According to one aspect, an intelligent device wearing detection method is provided, where an intelligent device includes a first sensor and a second sensor. The method includes obtaining a measurement value of the first sensor, when the measurement value of the first sensor is greater than a first threshold, determining that the intelligent device is in a worn state, when the measurement value of the first sensor is less than a second threshold, determining that the intelligent device is in a not-worn state, where the first threshold is greater than the second threshold, and when the measurement value of the first sensor is greater than and/or equal to the second threshold, and less than and/or equal to the first threshold, turning on the second sensor, obtaining a measurement value of the second sensor, and determining, based on the measurement value of the second sensor, that the intelligent device is in a worn state and/or in a not-worn state.

In an embodiment of the present invention, data detected by a plurality of sensors on the intelligent device is combined for wearing detection. The first sensor is first used for wearing detection, and the first sensor may be but not limited to a capacitive sensor with low power consumption. When the capacitive sensor cannot make accurate determining, another sensor with high power consumption is then used for wearing detection. This improves wearing detection accuracy and optimizes power consumption for wearing detection.

In a possible implementation, the first sensor is a capacitive sensor, the second sensor is an infrared sensor, and the method includes when a measurement value of the infrared sensor is greater than and/or equal to a third threshold, and less than and/or equal to a fourth threshold, determining that the intelligent device is in a worn state, where the third threshold is less than the fourth threshold, or when the measurement value of the infrared sensor is greater than the fourth threshold, and/or when the measurement value of the infrared sensor is less than the third threshold, determining that the intelligent device is in a not-worn state.

In an embodiment of the present invention, a specific type of the first sensor and that of the second sensor are provided. The capacitive sensor has relatively low power consumption and cannot determine, based on some measurement values, whether the intelligent device is in a worn state. Therefore, the measurement value of the infrared sensor is referenced to determine whether the intelligent device is in a worn state. This can improve wearing detection accuracy and reduce power consumption for wearing detection.

In a possible implementation, the first sensor is a capacitive sensor, and the second sensor is a heart rate detection sensor. The method includes when a measurement value of the heart rate detection sensor is greater than and/or equal to a fifth threshold, and less than and/or equal to a sixth threshold, determining that the intelligent device is in a worn state, where the fifth threshold is less than the sixth threshold, or when the measurement value of the heart rate detection sensor is greater than the sixth threshold, and/or when the measurement value of the heart rate detection sensor is less than the fifth threshold, determining that the intelligent device is in a not-worn state.

In an embodiment of the present invention, a specific type of the first sensor and that of the second sensor are provided.

The capacitive sensor has relatively low power consumption and cannot determine, based on some measurement values, whether the intelligent device is in a worn state. Therefore, the measurement value of the heart rate detection sensor is referenced to determine whether the intelligent device is in a worn state. This can improve wearing detection accuracy and reduce power consumption for wearing detection.

In a possible implementation, the first sensor is a capacitive sensor, the second sensor is a body temperature detection sensor. The method includes when a measurement value of the body temperature detection sensor is greater than and/or equal to a seventh threshold, and less than and/or equal to an eighth threshold, determining that the intelligent device is in a worn state, where the seventh threshold is less than the eighth threshold, or when the measurement value of the body temperature detection sensor is greater than the eighth threshold, and/or when the measurement value of the body temperature detection sensor is less than the seventh threshold, determining that the intelligent device is in a not-worn state.

In an embodiment of the present invention, a specific type of the first sensor and that of the second sensor are provided. The capacitive sensor has relatively low power consumption and cannot determine, based on some measurement values, whether the intelligent device is in a worn state. Therefore, the measurement value of the body temperature detection sensor is referenced to determine whether the intelligent device is in a worn state. This can improve wearing detection accuracy and reduce power consumption for wearing detection.

In a possible implementation, before the obtaining a measurement value of the first sensor, the method further includes determining a current status of the intelligent device, where the status is one of a power-on initial state, a not-worn state, and a worn state, when determining that the status is a not-worn state, determining that an increased value of the measurement value of the capacitive sensor in first preset duration is greater than a ninth threshold, and when determining that the status is a worn state, determining that a decreased value of the measurement value of the capacitive sensor in second preset duration is greater than a tenth threshold.

In an embodiment of the present invention, a current status of the intelligent device is determined, so as to optimize a wearing detection algorithm and further improve wearing detection accuracy. A put-on action triggers an obvious rising edge value of readings of the first sensor, and a device take-off action triggers an obvious falling edge value of the readings of the first sensor. Therefore, the device put-on action and the device take-off action can be accurately detected by determining a rising edge and a falling edge of the measurement value. After the device put-on action and the device take-off action are detected, a worn state and/or a not-worn state are/is determined. This can further improve wearing detection accuracy.

In a possible implementation, when the status is determined to be a worn state, that fast take-off action detection is not required is determined based on configuration information of an application enabled on the intelligent device.

In an embodiment of the present invention, for a characteristic that a detection time of the first sensor may be longer, when the current status is determined to be a worn state, that fast take-off action detection is not required is first determined, and a corresponding detection method is then executed. This can also satisfy a user requirement when fast take-off action detection is required.

In a possible implementation, the intelligent device further includes a third sensor, and the third sensor is an acceleration sensor. The method further includes obtaining a measurement value of the acceleration sensor in third preset duration, and when the measurement value of the acceleration sensor in the third preset duration is less than an eleventh threshold, determining that the intelligent device is in a not-worn state.

In an embodiment of the present invention, that the intelligent device is in a not-worn state may be accurately determined by using long-term data of the acceleration sensor, so as to correct a detection result of the first sensor and/or the second sensor and improve wearing detection accuracy.

In a possible implementation, after that the intelligent device is in a worn state and/or in a not-worn state is determined based on the measurement value of the second sensor, the second sensor is turned off.

In an embodiment of the present invention, the second sensor is turned off after the second sensor is used, so that power consumption can be effectively reduced.

According to another aspect, an intelligent device is provided. The intelligent device may implement functions executed by the intelligent device in the foregoing method examples. The functions may be implemented by hardware or by corresponding software executed by the hardware. The hardware and/or software include(s) a unit and/or a module corresponding to one and/or more of the foregoing functions.

In a possible design, a structure of the intelligent device includes a processor, a first sensor, and a second sensor. The processor is configured to support the intelligent device to execute corresponding functions in the foregoing method. The first sensor and the second sensor are configured to obtain a measurement value. The intelligent device further includes a memory. The memory is configured to be coupled to the processor, and the memory stores a necessary program instruction and data for the intelligent device.

According to still another aspect, an embodiment of the present invention provides a computer storage medium, configured to store a computer software instruction used by the foregoing intelligent device, including an instruction used to execute a program designed by the foregoing aspect.

Compared with the prior art, in the intelligent device wearing detection method provided by the embodiments of the present invention, data detected by the plurality of sensors on the intelligent device is combined for wearing detection. The first sensor with low power consumption is first used for wearing detection. When the first sensor cannot make accurate determining, another sensor with high power consumption is then used for wearing detection. This improves wearing detection accuracy and optimizes power consumption for wearing detection.

DETAILED DESCRIPTION OF ILLUSTRATIVE EMBODIMENTS

Figure 1A:
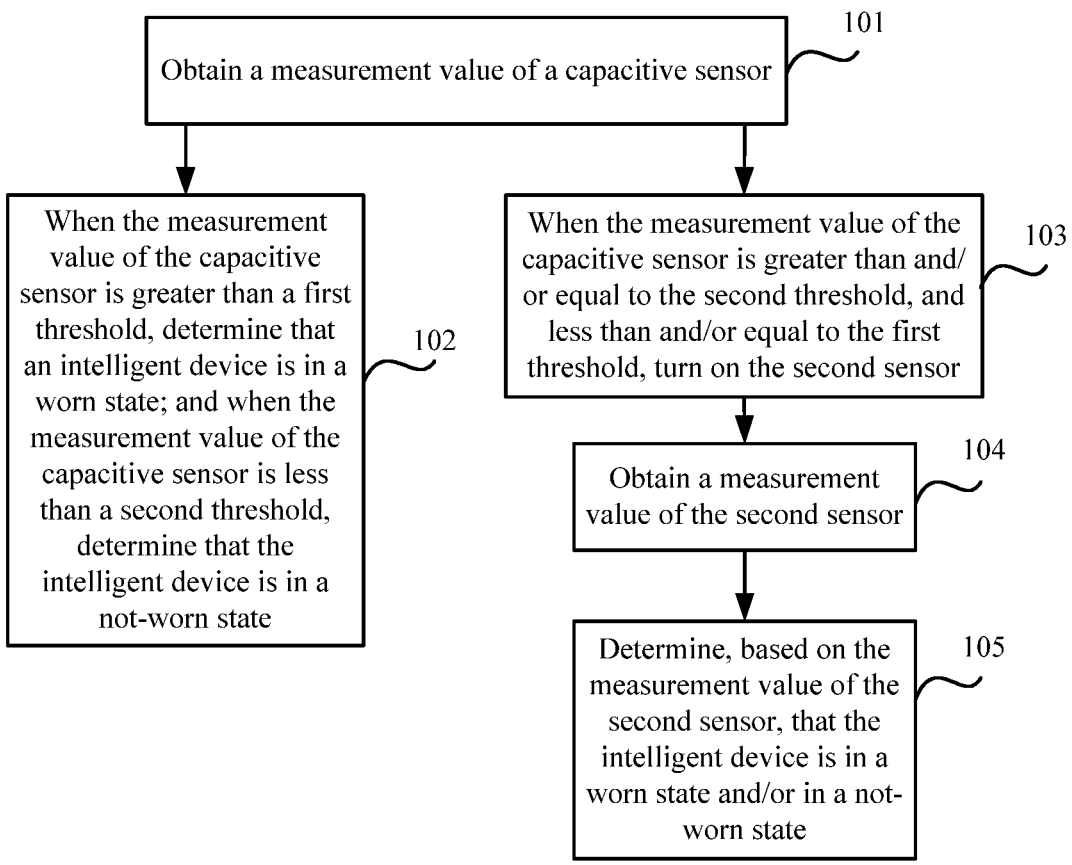
FIG. 1A is a flowchart of an intelligent device wearing detection method according to an embodiment of the present invention.

To make the objectives, technical solutions, and advantages of the embodiments of the present invention clearer, the following describes the technical solutions in the embodiments of the present invention with reference to the accompanying drawings in the embodiments of the present invention. Apparently, the described embodiments are a part rather than all of the embodiments of the present invention. All other embodiments obtained by a person of ordinary skill in the art based on the embodiments of the present invention without creative efforts shall fall within the protection scope of the present invention.

In the embodiments of the present invention, there are mainly three types of sensors: a capacitive sensor (CAP Sensor), an infrared sensor (IR Sensor), and an acceleration sensor (A-Sensor). PPG components used by an intelligent device usually include two parts: a green light part and an infrared light part. The infrared light part may be used for wearing detection. The following briefly describes the three types of sensors. The capacitive sensor measures different capacitive values when the device is worn and/or not worn, so as to differentiate, based on the capacitive values, a worn state and/or a not-worn state, and/or detect, based on a change of the capacitive values, a device put-on action and/or a device take-off action. The infrared sensor measures an IR reflected light intensity when the device comes in contact with different objects, so as to differentiate, based on different reflected light intensities, whether the device is in a worn state. The acceleration sensor measures accelerations in three directions of X, Y, and Z axises, so as to calculate an acceleration sum and differentiate, based on differences between acceleration sums when the device is worn and those when the device is not worn, whether the device is in a worn state.

Data is collected for the capacitive sensor and the infrared sensor through an experiment. Experimental data is obtained and analyzed, so as to obtain characteristics of some measurement values of the capacitive sensor and the infrared sensor. The experiment is specifically as follows.

Sample analysis is performed on CAP sensor data and IR data. A sample device with a CAP sensor and an IR sensor is used, and data of reading values of the CAP sensor and reading values of the IR sensor is collected in different scenarios.

CAP sensor data collection scenarios include collecting CAP sensor data when the sample device is loosely worn, collecting CAP sensor data when the sample device is tightly worn, and collecting CAP sensor data when the sample device is not worn and is placed on different materials in a sidelong manner, a bottom coming in contact with different materials, where these materials include paper, wooden table, glass, plastics, iron sheet, leather, and cotton cloth. The CAP sensor data is collected when the sample device is put on and taken off successively for a plurality of times.

Based on analysis of the collected CAP sensor data in these scenarios, the following regularities are summarized: (1) A device put-on action and a device take-off action can be accurately detected by determining a rising edge and a falling edge of readings of the CAP sensor. A put-on action may trigger an obvious rising edge value of the readings of the CAP sensor, and taking off the device may trigger an obvious falling edge value of the readings of the CAP sensor. (2) There is a specific degree of differentiation between a CAP value when the device is tightly worn and that when the device is not worn. However, there is a relatively small degree of differentiation between the CAP value when the device is tightly worn and that when the device is placed on an iron sheet, therefore, there is a probability of incorrect detection when a wearing status is determined based on the CAP value in this scenario. (3) There is a coincidence between a CAP value when the device is loosely worn and that when the device is not worn, and whether the device is worn cannot be determined.

IR data collection scenarios include measuring a reading value of IR reflected light intensity when the device is worn with different tightness, where different tightness includes several scenarios such as making a bottom of the sample device close to skin and separately keeping the bottom of the sample device 0.5 cm, 1 cm, or 1.5 cm away from skin, the sample device is not worn but hung in the air, when the sample device is not worn, and the bottom of the sample device comes in contact with different materials closely or 2 mm away from the materials, where these different materials include several scenarios of wooden table, paper, plastics, glass, and iron sheet.

The following regularities are summarized by analyzing the collected IR data in these scenarios: IR data distribution is basically stable and basically falls within a normal wearing range when the device is worn in a stable state but worn with different tightness, there is a relatively good degree of differentiation between IR data in a worn-state scenario and that in a not-worn-state scenario.

In the embodiments of the present invention, based on the characteristics of the measurement value of the capacitive sensor, the capacitive sensor is used in combination with the infrared sensor for wearing detection, and/or the capacitive sensor is used in combination with another type of sensor for wearing detection, so as to improve wearing detection accuracy and reduce power consumption for wearing detection.

It should be understood that ordinal numbers such as "first" and "second" mentioned in the embodiments of the present invention should be construed as merely for distinguishing, unless otherwise determined, based on a context, as definitely representing an order.

In the embodiments of the present invention, that the first sensor is a capacitive sensor is merely used for description, but does not set a limitation on a type of the first sensor.

FIG. 1A is a flowchart of an intelligent device wearing detection method according to an embodiment of the present invention. An intelligent device includes a first sensor and a second sensor. The first sensor is a capacitive sensor, and the second sensor is another type of sensor, for example, an infrared sensor, a heart rate detection sensor, and/or a body temperature detection sensor. The method includes the following steps.

Step 101: Obtain a measurement value of the capacitive sensor.

Specifically, a plurality of readings of the capacitive sensor in preset duration may be read, and then an average value of these readings is obtained. The average value is used as the measurement value of the capacitive sensor.

Step 102: When the measurement value of the capacitive sensor is greater than a first threshold, determine that the intelligent device is in a worn state, and when the measurement value of the capacitive sensor is less than a second threshold, determine that the intelligent device is in a not-worn state, where the first threshold is greater than the second threshold.

In this embodiment of the present invention, specific values of the first threshold and the second threshold may be predetermined through an experiment. The first threshold is a critical value that can be used to accurately determine, based on the measurement value of the capacitive sensor, that the intelligent device is in a worn state. The second threshold is a critical value that can be used to accurately determine, based on the measurement value of the capacitive sensor, that the intelligent device is in a not-worn state.

Step 103: When the measurement value of the capacitive sensor is greater than and/or equal to the second threshold, and less than and/or equal to the first threshold, turn on the second sensor.

When the measurement value of the capacitive sensor is greater than and/or equal to the second threshold, and less than and/or equal to the first threshold, whether the intelligent device is in a worn state cannot be accurately determined based on the measurement value of the capacitive sensor. In this case, the second sensor is then turned on. Before this, the second sensor is in an off state.

Step 104: Obtain a measurement value of the second sensor.

A reading of the second sensor at a moment may be read, and the reading is used as the measurement value of the second sensor. Alternatively, a plurality of readings of the second sensor in preset duration may be read, and then an average value of these readings is obtained. The average value is used as the measurement value of the second sensor.

Step 105: Determine, based on the measurement value of the second sensor, that the intelligent device is in a worn state and/or in a not-worn state.

The second sensor may be turned off after that the intelligent device is in a worn state and/or in a not-worn state is determined.

In one example, the second sensor is an infrared sensor. When a measurement value of the infrared sensor is greater than and/or equal to a third threshold, and less than and/or equal to a fourth threshold, that the intelligent device is in a worn state is determined, where the third threshold is less than the fourth threshold. When the measurement value of the infrared sensor is greater than the fourth threshold, and/or when the measurement value of the infrared sensor is less than the third threshold, that the intelligent device is in a not-worn state is determined.

In this embodiment of the present invention, specific values of the third threshold and the fourth threshold may be predetermined through an experiment. The third threshold is a lower limit that can be used to accurately determine, based on the measurement value of the infrared sensor, that the intelligent device is in a worn state. The fourth threshold is an upper limit that can be used to accurately determine, based on the measurement value of the infrared sensor, that the intelligent device is in a worn state.

In another example, the second sensor is a heart rate detection sensor. When a measurement value of the heart rate detection sensor is greater than and/or equal to a fifth threshold, and less than and/or equal to a sixth threshold, that the intelligent device is in a worn state is determined, where the fifth threshold is less than the sixth threshold, or when the measurement value of the heart rate detection sensor is greater than the sixth threshold, and/or when the measurement value of the heart rate detection sensor is less than the fifth threshold, that the intelligent device is in a not-worn state is determined.

In this embodiment of the present invention, specific values of the fifth threshold and the sixth threshold may be determined based on a normal range of human heart rates. For example, the fifth threshold is 40 times/minute, and the sixth threshold is 160 times/minute.

In another example, the second sensor is a body temperature detection sensor. When a measurement value of the body temperature detection sensor is greater than and/or equal to a seventh threshold, and less than and/or equal to an eighth threshold, that the intelligent device is in a worn state is determined, where the seventh threshold is less than the eighth threshold, or when the measurement value of the body temperature detection sensor is greater than the eighth threshold, and/or when the measurement value of the body temperature detection sensor is less than the seventh threshold, that the intelligent device is in a not-worn state is determined.

In this embodiment of the present invention, specific values of the seventh threshold and the eighth threshold may be determined based on a normal range of human body temperature. For example, the seventh threshold is 36° C., and the eighth threshold is 39° C.

In this embodiment of the present invention, a component with low power consumption is first used for preliminary wearing status detection. If the component with low power consumption cannot make accurate determining, a component with good stability and high accuracy is used for state determining. Therefore, power consumption for wearing detection is effectively reduced.

Figure 1B:
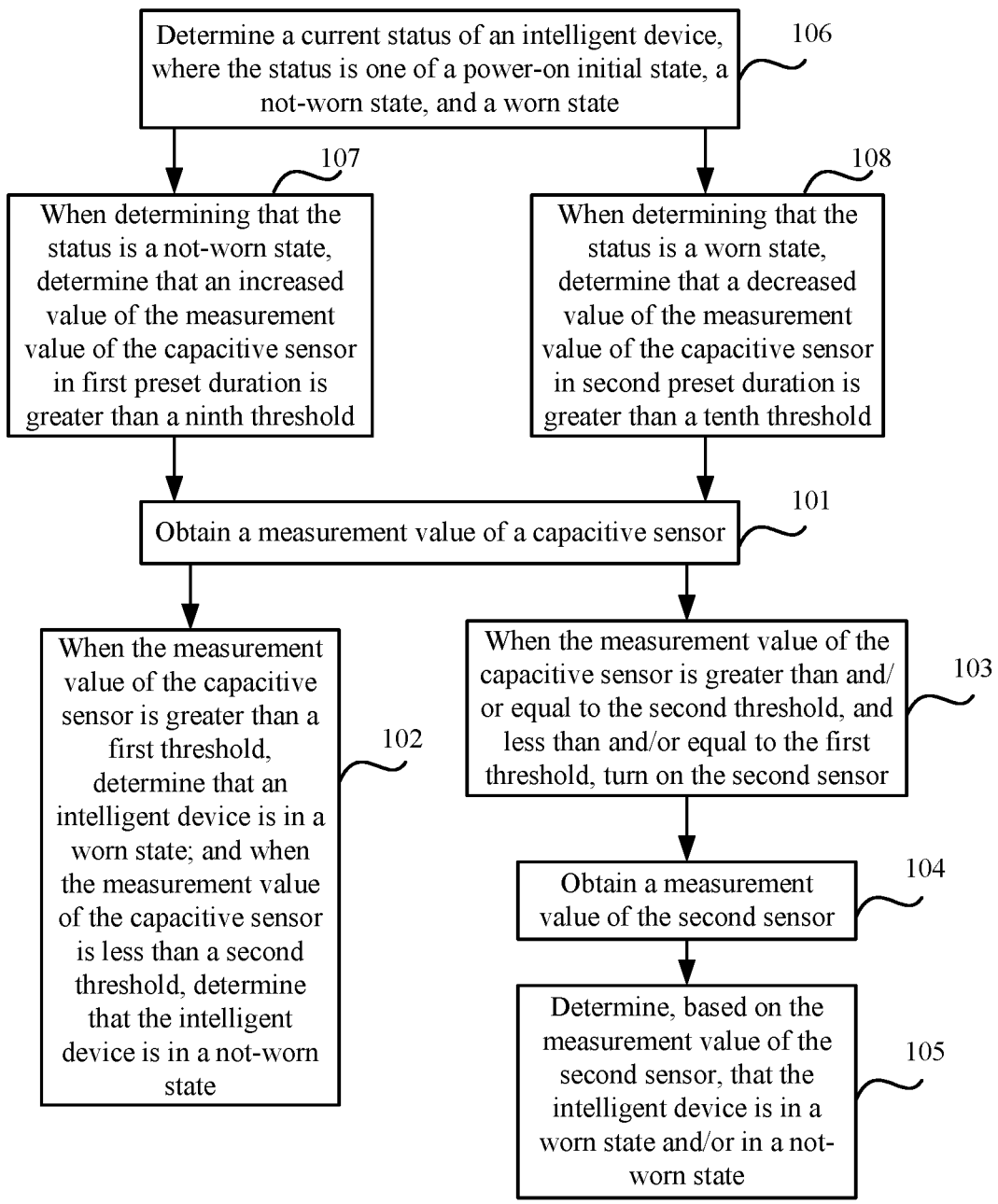
FIG. 1B is a flowchart of another intelligent device wearing detection method according to an embodiment of the present invention.

FIG. 1B is a flowchart of another intelligent device wearing detection method according to an embodiment of the present invention. In addition to the foregoing steps 101 to 105, the method further includes the following steps before step 101 is performed.

Step 106: Determine a current status of the intelligent device, where the status is one of a power-on initial state, a not-worn state, and a worn state.

Step 107: When determining that the status is a not-worn state, determine that an increased value of the measurement value of the capacitive sensor in first preset duration is greater than a ninth threshold.

In this embodiment of the present invention, specific values of the first preset duration and the ninth threshold may be predetermined through an experiment.

When a user makes a put-on action, the measurement value of the capacitive sensor has an upward transition. Therefore, after that the user makes the put-on action may be determined in the manner in step 107, whether the device is in a worn state is detected, so that accuracy is relatively high.

Step 108: When determining that the status is a worn state, determine that a decreased value of the measurement value of the capacitive sensor in second preset duration is greater than a tenth threshold.

In this embodiment of the present invention, specific values of the second preset duration and the tenth threshold may be predetermined through an experiment.

When the intelligent device is taken off, the measurement value of the capacitive sensor has a downward transition. Therefore, after that the intelligent device is taken off may be determined in the manner in step 108, whether the intelligent device is in a not-worn state is detected, so that accuracy is relatively high.

In addition, when that the status is a power-on initial state is determined, step 101 is directly performed.

Figure 1C:
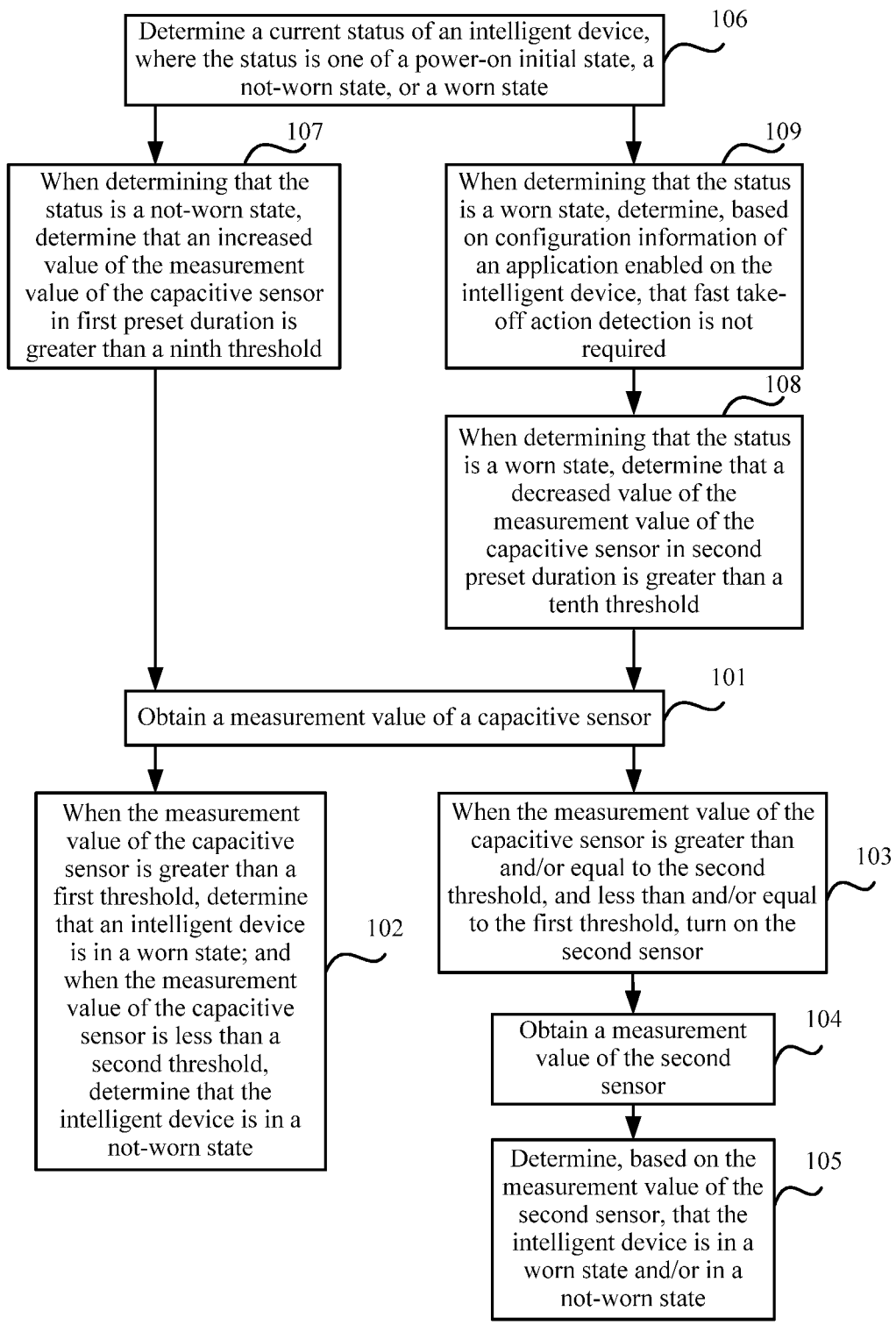
FIG. 1C is a flowchart of another intelligent device wearing detection method according to an embodiment of the present invention.

FIG. 1C is a flowchart of another intelligent device wearing detection method according to an embodiment of the present invention. In addition to the foregoing steps 101 to 108, the method further includes the following steps.

Step 109: When determining that the status is a worn state, determine, based on configuration information of an application enabled on the intelligent device, that fast take-off action detection is not required.

Based on different use scenarios, whether a process of fast take-off detection is required may be dynamically configured for an upper-layer application. A wearing detection algorithm may adapt to different detection performance requirements.

A detection speed of the capacitive sensor is relatively slow, and therefore, that fast take-off action detection is not required is first determined, and then whether the intelligent device is in a worn state is determined by using both the capacitive sensor and another sensor. When that fast take-off action detection is required is determined, the second sensor is directly turned on for detection, so as to meet a personalized requirement of the application.

Figure 1D:
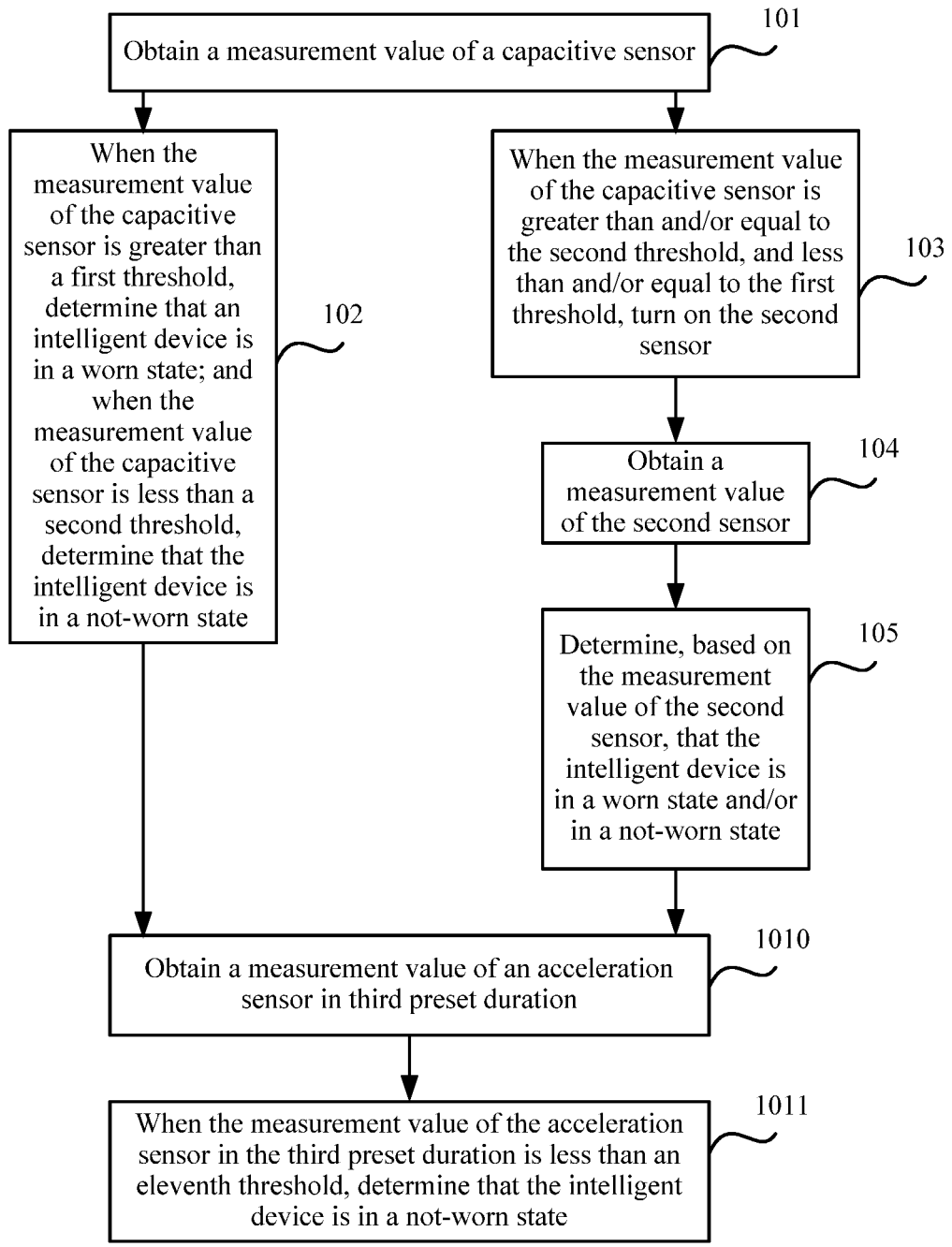
FIG. 1D is a flowchart of another intelligent device wearing detection method according to an embodiment of the present invention.

FIG. 1D is a flowchart of another intelligent device wearing detection method according to an embodiment of the present invention. In addition to the foregoing first sensor and the second sensor, the intelligent device further includes a third sensor, and the third sensor is an acceleration sensor. In addition to the foregoing steps 101 to 105, the method further includes the following.

Step 1010: Obtain a measurement value of the acceleration sensor in third preset duration.

A length of the third preset duration may be predetermined through an experiment.

Step 1011: When the measurement value of the acceleration sensor in the third preset duration is less than an eleventh threshold, determine that the intelligent device is in a not-worn state.

The eleventh threshold may be predetermined through an experiment.

In this embodiment of the present invention, that the intelligent device is in a not-worn state may be accurately determined by using long-term data of the acceleration sensor, so as to correct a detection result of the first sensor and/or the second sensor and improve wearing detection accuracy.

In addition, FIG. 1D is merely a possible embodiment provided by the present invention. A person skilled in the art may understand that there may also be an embodiment including steps 101 to 108 and steps 1010 and 1011, and an embodiment including steps 101 to 109 and steps 1010 and 1011.

Figure 2A:
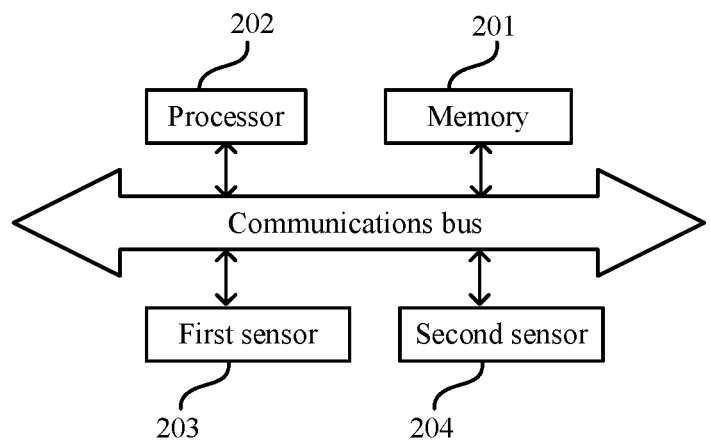
FIG. 2A is a structural diagram of an intelligent device according to an embodiment of the present invention.

FIG. 2A is a structural diagram of an intelligent device according to an embodiment of the present invention. The intelligent device is configured to perform the intelligent device wearing detection method provided by the embodiments of the present invention. The intelligent device includes a memory 201, a processor 202, a first sensor 203, and a second sensor 204. The first sensor 203 is a capacitive sensor.

The memory 201 is configured to store a program instruction.

The processor 202 is configured to perform the following operations based on the program instruction stored in the memory 201, including obtaining a measurement value of the capacitive sensor, when the measurement value of the capacitive sensor is greater than a first threshold, determining that the intelligent device is in a worn state, when the measurement value of the capacitive sensor is less than a second threshold, determining that the intelligent device is in a not-worn state, where the first threshold is greater than the second threshold, and when the measurement value of the capacitive sensor is greater than and/or equal to the second threshold, and less than and/or equal to the first threshold, turning on the second sensor 204, obtaining a measurement value of the second sensor 204, and determining, based on the measurement value of the second sensor 204, that the intelligent device is in a worn state and/or in a not-worn state.

In one example, the second sensor 204 is an infrared sensor. The operation, performed by the processor 202, of determining, based on the measurement value of the second sensor 204, that the intelligent device is in a worn state and/or in a not-worn state includes when a measurement value of the infrared sensor is greater than and/or equal to a third threshold, and less than and/or equal to a fourth threshold, determining that the intelligent device is in a worn state, where the third threshold is less than the fourth threshold, or when the measurement value of the infrared sensor is greater than the fourth threshold, and/or when the measurement value of the infrared sensor is less than the third threshold, determining that the intelligent device is in a not-worn state.

In another example, the second sensor 204 is a heart rate detection sensor. The operation, performed by the processor 202, of determining, based on the measurement value of the second sensor 204, that the intelligent device is in a worn state and/or in a not-worn state includes when a measurement value of the heart rate detection sensor is greater than and/or equal to a fifth threshold, and less than and/or equal to a sixth threshold, determining that the intelligent device is in a worn state, where the fifth threshold is less than the sixth threshold, or when the measurement value of the heart rate detection sensor is greater than the sixth threshold, and/or when the measurement value of the heart rate detection sensor is less than the fifth threshold, determining that the intelligent device is in a not-worn state.

In another example, the second sensor 204 is a body temperature detection sensor. The operation, performed by the processor 202, of determining, based on the measurement value of the second sensor 204, that the intelligent device is in a worn state and/or in a not-worn state includes when a measurement value of the body temperature detection sensor is greater than and/or equal to a seventh threshold, and less than and/or equal to an eighth threshold, determining that the intelligent device is in a worn state, where the seventh threshold is less than the eighth threshold, or when the measurement value of the body temperature detection sensor is greater than the eighth threshold, and/or when the measurement value of the body temperature detection sensor is less than the seventh threshold, determining that the intelligent device is in a not-worn state.

In one example, before performing the operation of obtaining the measurement value of the capacitive sensor, the processor 202 is further configured to perform the following operations based on the program instruction stored in the memory 201, including determining a current status of the intelligent device, where the status is one of a power-on initial state, a not-worn state, and a worn state, when determining that the status is a not-worn state, determining that an increased value of the measurement value of the capacitive sensor in first preset duration is greater than a ninth threshold, and when determining that the status is a worn state, determining that a decreased value of the measurement value of the capacitive sensor in second preset duration is greater than a tenth threshold.

In one example, the processor 202 is further configured to perform the following operation based on the program instruction stored in the memory 201, including when determining that the status is a worn state, determining, based on configuration information of an application enabled on the intelligent device, that fast take-off action detection is not required.

Figure 2B:
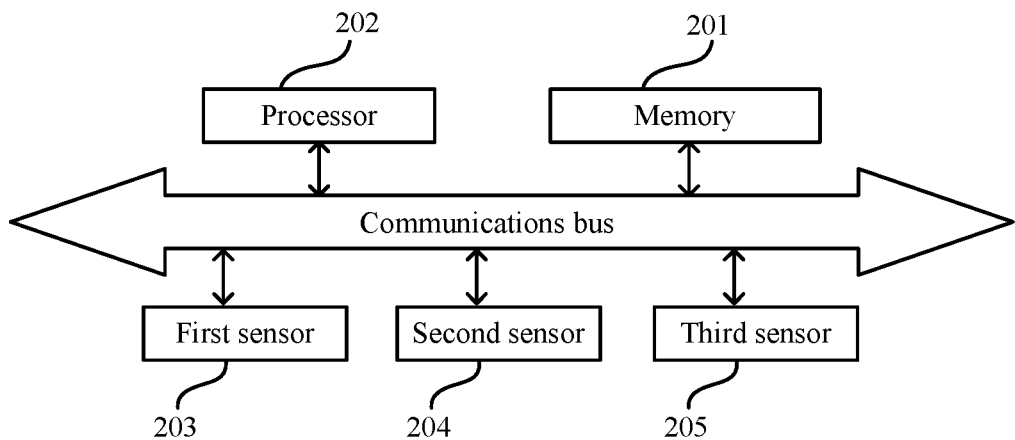
FIG. 2B is a structural diagram of another intelligent device according to an embodiment of the present invention.

Referring to FIG. 2B, in one example, the intelligent device further includes a third sensor 205, and the third sensor 205 is an acceleration sensor. The processor 202 is further configured to perform the following operations based on the program instruction stored in the memory 201, including obtaining a measurement value of the acceleration sensor in third preset duration, and when the measurement value of the acceleration sensor in the third preset duration is less than an eleventh threshold, determining that the intelligent device is in a not-worn state.

Referring to FIG. 2A and/or FIG. 2B, in one example, after performing the operation of determining, based on the measurement value of the second sensor 204, that the intelligent device is in a worn state and/or in a not-worn state, the processor 202 is further configured to perform the following operation based on the program instruction stored in the memory 201, including turning off the second sensor 204.

Figure 2C:
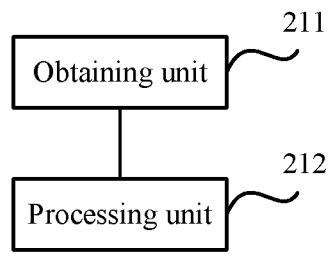
FIG. 2C is a structural diagram of another intelligent device according to an embodiment of the present invention.

FIG. 2C is a structural diagram of another intelligent device according to an embodiment of the present invention. The intelligent device is configured to perform the intelligent device wearing detection method provided by the embodiments of the present invention. The intelligent device includes a first sensor and a second sensor, and the first sensor is a capacitive sensor. The intelligent device further includes an obtaining unit 211, configured to obtain a measurement value of the capacitive sensor, and a processing unit 212, configured to when the measurement value of the capacitive sensor obtained by the obtaining unit 211 is greater than a first threshold, determine that the intelligent device is in a worn state, when the measurement value of the capacitive sensor is less than a second threshold, determine that the intelligent device is in a not-worn state, where the first threshold is greater than the second threshold, and when the measurement value of the capacitive sensor is greater than and/or equal to the second threshold, and less than and/or equal to the first threshold, turn on the second sensor.

The obtaining unit 211 is further configured to obtain a measurement value of the second sensor.

The processing unit 212 is further configured to determine, based on the measurement value of the second sensor obtained by the obtaining unit 211, that the intelligent device is in a worn state and/or in a not-worn state.

In one example, the second sensor is an infrared sensor.

The processing unit 212 is specifically configured to when a measurement value of the infrared sensor obtained by the obtaining unit 211 is greater than and/or equal to a third threshold, and less than and/or equal to a fourth threshold, determine that the intelligent device is in a worn state, where the third threshold is less than the fourth threshold, or when the measurement value of the infrared sensor obtained by the obtaining unit 211 is greater than the fourth threshold, and/or when the measurement value of the infrared sensor obtained by the obtaining unit 211 is less than the third threshold, determine that the intelligent device is in a not-worn state.

In one example, the second sensor is a heart rate detection sensor.

The processing unit 212 is specifically configured to when a measurement value of the heart rate detection sensor obtained by the obtaining unit 211 is greater than and/or equal to a fifth threshold, and less than and/or equal to a sixth threshold, determine that the intelligent device is in a worn state, where the fifth threshold is less than the sixth threshold, or when the measurement value of the heart rate detection sensor obtained by the obtaining unit 211 is greater than the sixth threshold, and/or when the measurement value of the heart rate detection sensor is less than the fifth threshold, determine that the intelligent device is in a not-worn state.

In one example, the second sensor is a body temperature detection sensor.

The processing unit 212 is specifically configured to when a measurement value of the body temperature detection sensor obtained by the obtaining unit 211 is greater than and/or equal to a seventh threshold, and less than and/or equal to an eighth threshold, determine that the intelligent device is in a worn state, where the seventh threshold is less than the eighth threshold, or when the measurement value of the body temperature detection sensor obtained by the obtaining unit 211 is greater than the eighth threshold, and/or when the measurement value of the body temperature detection sensor obtained by the obtaining unit 211 is less than the seventh threshold, determine that the intelligent device is in a not-worn state.

In one example, the processing unit 212 is further configured to before the obtaining unit 211 obtains the measurement value of the capacitive sensor, determine a current status of the intelligent device, where the status is one of a power-on initial state, a not-worn state, and a worn state, when determining that the status is a not-worn state, determine that an increased value of the measurement value of the capacitive sensor in first preset duration is greater than a ninth threshold, and when determining that the status is a worn state, determine that a decreased value of the measurement value of the capacitive sensor in second preset duration is greater than a tenth threshold.

In one example, the processing unit 212 is further configured to when the status is determined to be a worn state, determine, based on configuration information of an application enabled on the intelligent device, that fast take-off action detection is not required.

In one example, the intelligent device further includes a third sensor, and the third sensor is an acceleration sensor.

The obtaining unit 211 is further configured to obtain a measurement value of the acceleration sensor in third preset duration.

The processing unit 212 is further configured to when the measurement value of the acceleration sensor in the third preset duration is less than an eleventh threshold, determine that the intelligent device is in a not-worn state.

In one example, the processing unit 212 is further configured to after determining, based on the measurement value of the second sensor, that the intelligent device is in a worn state and/or in a not-worn state, turn off the second sensor.

The following describes in detail, by using a specific embodiment, an intelligent device wearing detection method provided by the present invention. In this embodiment, data detected by a plurality of sensors on a wearable intelligent device is combined for wearing detection. In different scenarios, using different sensors for detection and determining improves wearing detection accuracy, reduces power consumption for wearing detection, and enhances user experience in various use and wearing detection scenarios.

The following wearing detection scenarios are included in the present invention, including power-on initial-state detection, detection in a not-worn state, and detection in a worn state.

Based on different specific use scenarios of a device, the detection in a worn state is further divided into two scenarios, including a scenario with a fast take-off detection requirement and a scenario without a fast take-off detection requirement.

Figure 3:
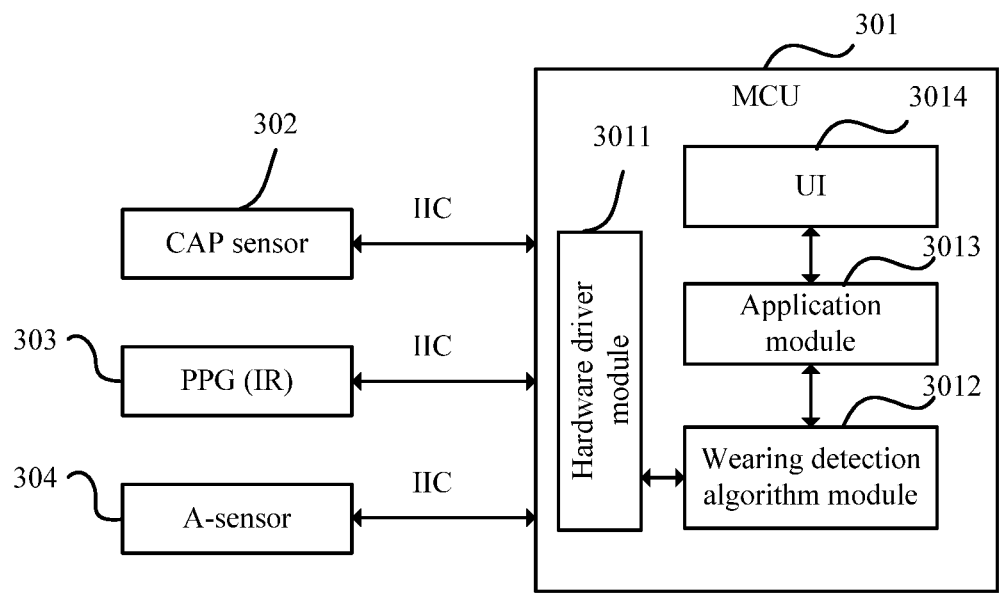
FIG. 3 is a schematic structural diagram of another intelligent device according to an embodiment of the present invention.

FIG. 3 is a structural diagram of another intelligent device according to an embodiment of the present invention. The intelligent device includes a microcontroller unit (MCU) 301, a capacitive sensor (CAP Sensor) 302, an infrared (IR) sensor 303, and an acceleration sensor (A-Sensor) 304. The IR sensor 303 is specifically an IR sensor part of a photoplethysmogram (PPG) sensor, and the MCU 301 includes a hardware driver module 3011, a wearing detection algorithm module 3012, an application module 3013, and a user interface (UI) 3014. In this embodiment of the present invention, each sensor is connected to and communicates with the MCU 301 by using a two-wire serial bus (Inter-Integrated Circuit, IIC). During initialization, the MCU 301 configures operating parameters of each sensor, for example, configures a sampling frequency of the CAP sensor 302 and/or the PPG (IR) 303 and/or the A-sensor 304, and a transmit current intensity and a gain of the IR 303. Each sensor is responsible for data collection, data operation and result outputting are both performed on the MCU 301.

Software of the MCU 301 controls turn-on and turn-off of each sensor based on a scenario logic of the application module 3013. The scenario logic herein includes the following. To determine a power-on initial state, turn on the CAP sensor 302 for initial-state detection, when a status cannot be accurately determined by using a reading of the CAP sensor 302, turn on the IR 303 for status determining, and turn off the IR 303 after the determining is complete, in a not-worn state, use a same logic to detect whether a put-on action occurs, in a worn state, if fast take-off detection is not required, use a logic same as that for the not-worn state to detect whether a take-off action occurs, and if fast take-off detection is required, turn off the CAP sensor 302 and perform take-off action determining by using a reading value of the IR 303 only. The A-sensor 304 is usually configured to collect user exercise data, and is in a steady-on state.

The sensor periodically collects data based on a configured data sampling frequency, and uploads the collected data to an internal software processing module of the MCU 301 by using the IIC bus. The software processing module is specifically a wearing detection algorithm module 3012. The wearing detection algorithm module 3012 obtains sensor data from bottom-layer hardware, runs an algorithm logic, and outputs a worn state and/or a not-worn state of the device. The application module 3013 obtains information about the worn state and/or the not-worn state of the device by using a software interface connecting to the wearing detection algorithm module 3012, and displays different UIs 3014 to a user based on such information. The wearing detection algorithm module 3012 and the application module 3013 and/or the UI 3014 may run on a same MCU processor or different processors. When running on different processors, the wearing detection algorithm module 3012 and the application module 3013 transfer status information by using an inter-core communications mechanism between the processors.

Based on analysis of data collected in an experiment, the sensors are designed to cooperatively perform a wearing detection algorithm procedure. In terms of power consumption, different configuration parameters of the sensors generate different power consumption, generally, power consumption of the CAP sensor is far lower than that of the IR sensor. This is also an important factor considered for optimizing power consumption in the algorithm solution. Therefore, in most scenarios of this embodiment of the present invention, the CAP sensor is first used for detection, and when that the intelligent device is in a worn state or in a not-worn state cannot be accurately determined by using a reading of the CAP sensor, the IR sensor is then used for detection. Refer to Table 1 showing a correspondence table between scenarios and wearing detection algorithms.

TABLE 1

| | |
|---|---|
| Initial-state detection | Turn on the CAP sensor and turn off the IR sensor. Turn on the IR sensor for determining when the CAP sensor cannot perform accurate detection, and turn off the IR sensor when the determining is completed. |
| Detection in a not-worn state | Turn on the CAP sensor and turn off the IR sensor. Turn on the IR sensor for determining when the CAP sensor cannot perform accurate detection, and turn off the IR sensor when the determining is completed. |
| Detection in a worn state | Fast take-off action detection is not required: Turn on the CAP sensor and turn off the IR sensor. Turn on the IR sensor for determining when the CAP sensor cannot perform accurate detection, and turn off the IR sensor when the determining is completed. Fast take-off action detection is not required: Turn off the CAP sensor, and turn on the IR sensor for detection. |

It can be learned from Table 1 that a specific wearing detection algorithm in use is related to a scenario in which the intelligent device is located, and/or that a specific wearing detection algorithm in use is related to a current status of the intelligent device.

Figure 4:
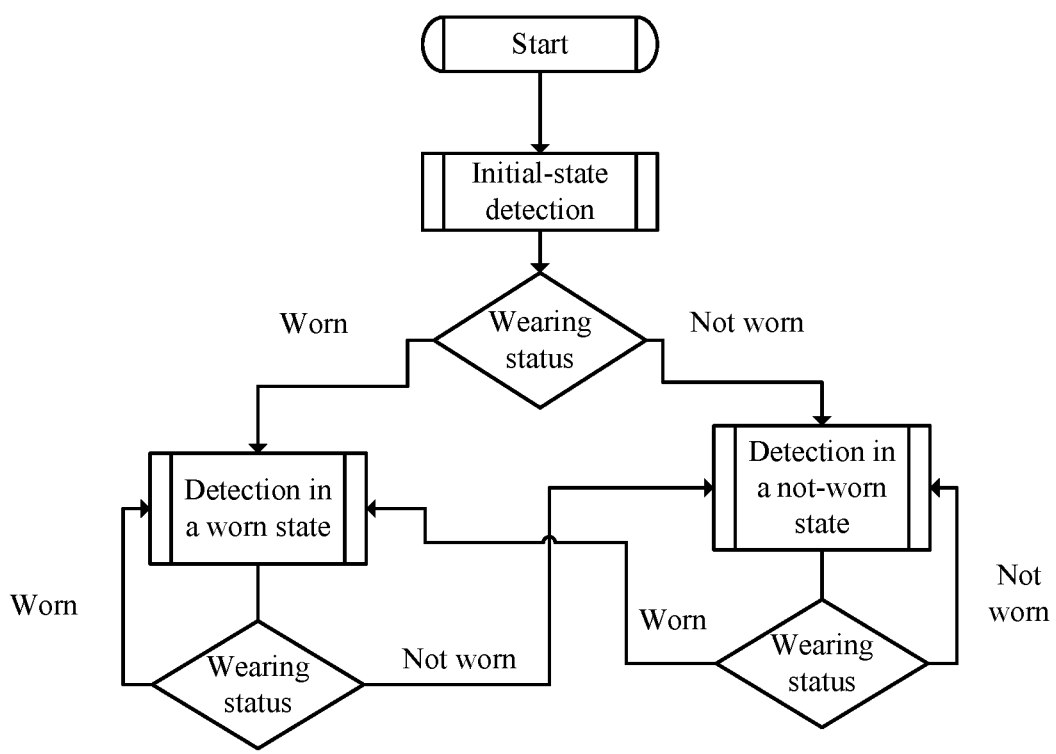
FIG. 4 is an overall schematic flowchart of wearing detection according to an embodiment of the present invention.

FIG. 4 is an overall schematic flowchart of wearing detection according to an embodiment of the present invention. Initial-state detection is performed upon power-on. A detection procedure in a worn state and/or in a not-worn state is executed based on an initial-state detection result of the worn state and/or the not-worn state.

Figure 5:
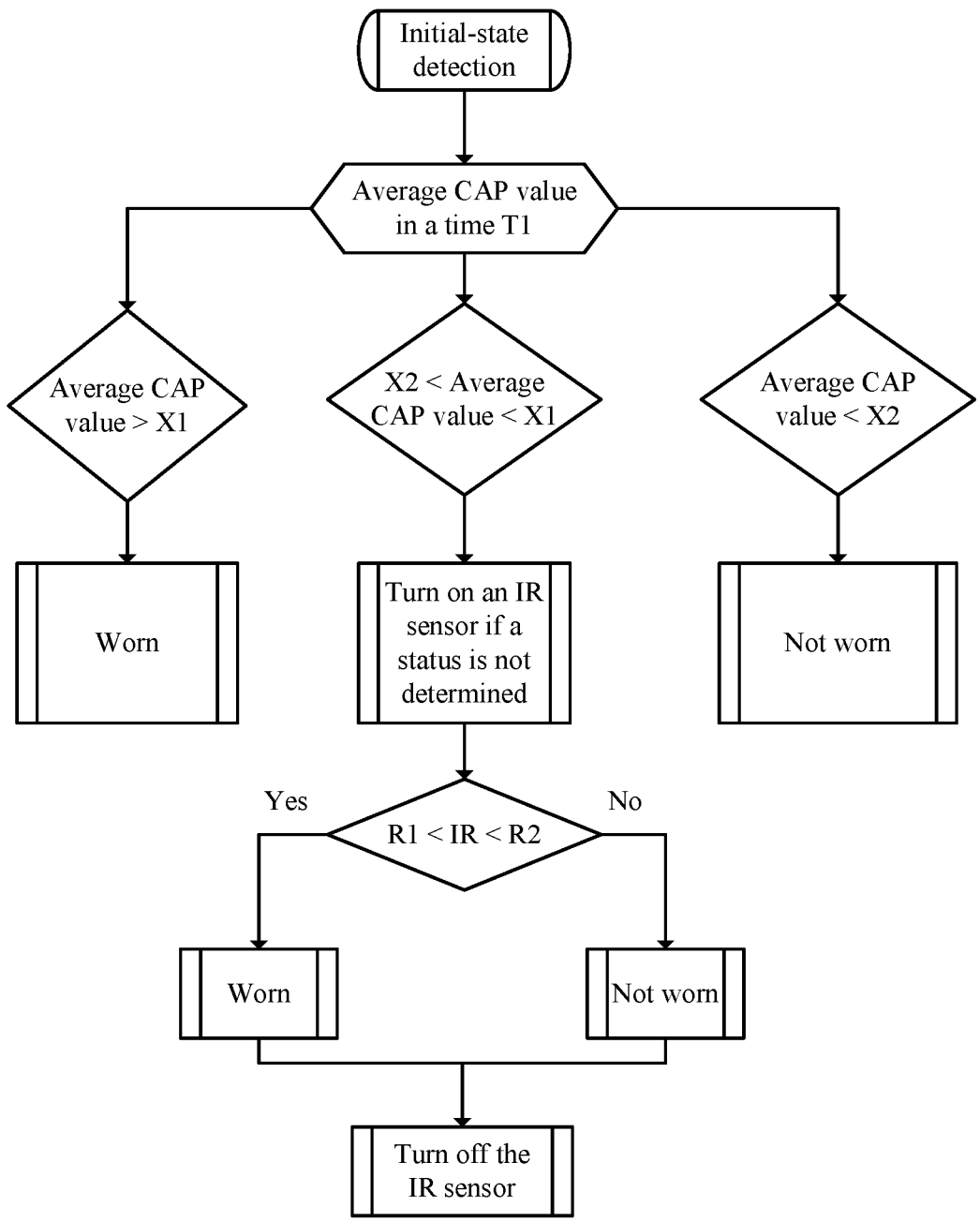
FIG. 5 is a schematic flowchart of initial-state detection according to an embodiment of the present invention.

FIG. 5 is a schematic flowchart of initial-state detection according to an embodiment of the present invention. In an initial state, a CAP sensor is turned on for detection. The CAP sensor directly outputs a worn state when an average reading value of the CAP sensor is greater than an absolute worn-state threshold X1. The CAP sensor directly outputs a not-worn state when the average reading value of the CAP sensor is less than an absolute not-worn-state threshold X2. When the average reading value of the CAP sensor ranges from X2 to X1 and the wearing status cannot be accurately determined, in this case, an IR sensor is turned on for wearing detection. A worn state is output when a reading value of the IR sensor is within a wearing threshold range [R1, R2], a not-worn state is output when a reading value of the IR sensor is beyond the wearing threshold range [R1, R2].

Considering impact of factors such as a CAP sensor component selected for the device and a device bottom housing material, the average value thresholds X1 and X2 of the CAP sensor that are selected by different devices have relatively great differences. Similarly, the reading value of the IR sensor is also related to a component in use. The thresholds R1 and R2 of the IR sensor for different devices also have relatively great differences. The foregoing thresholds may be determined based on an analysis result of data collected by a sampling device.

Figure 6:
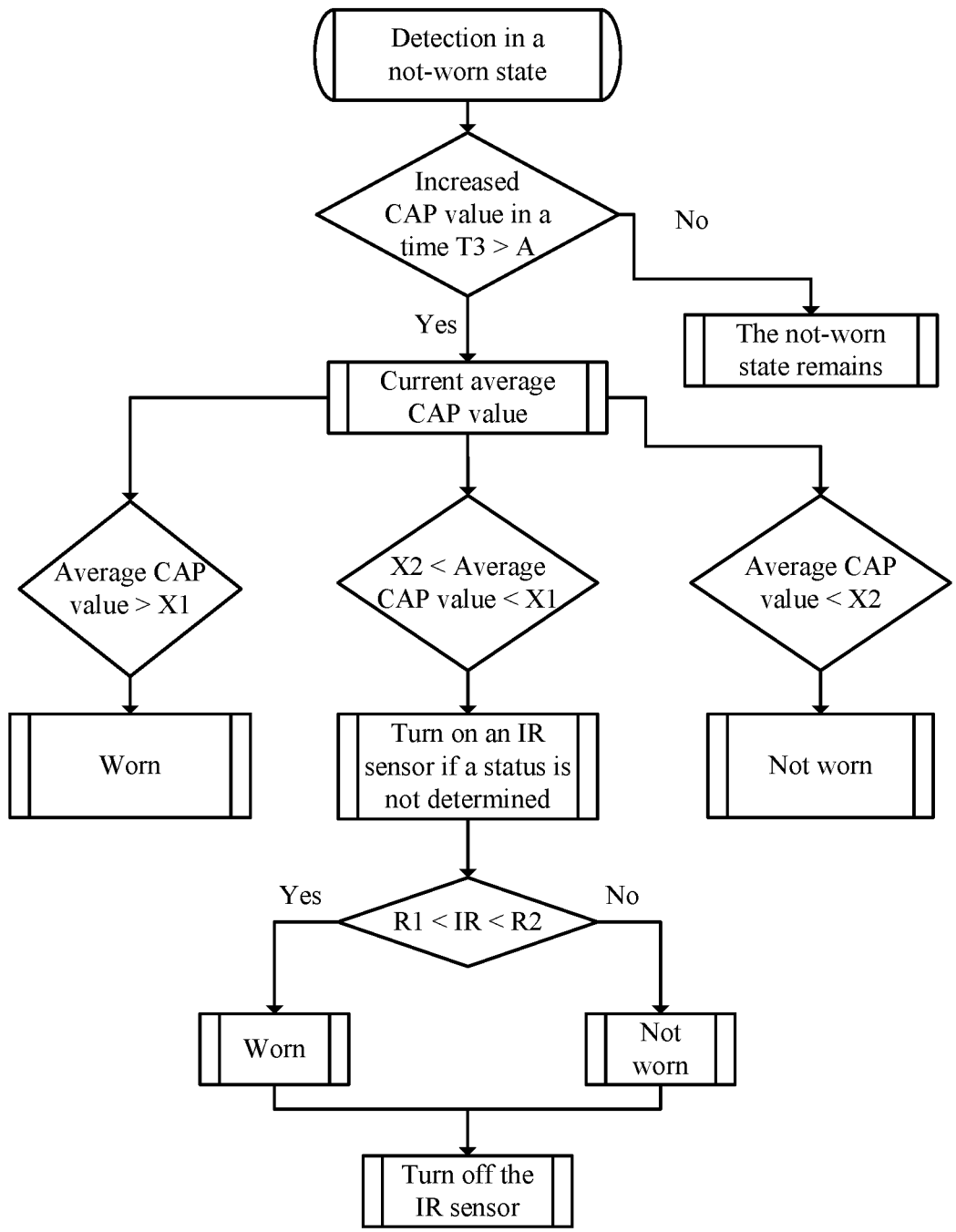
FIG. 6 is a schematic flowchart of detection in a not-worn state according to an embodiment of the present invention.

FIG. 6 is a schematic flowchart of detection in a not-worn state according to an embodiment of the present invention. In the not-worn state, whether a device put-on action occurs is mainly detected, and a triggering state is that the not-worn state turns to a worn state. Specifically, whether a reading value of a CAP sensor has an upward transition is detected. If an upward transition occurs, a put-on action may occur. If a case that a put-on action may be triggered is detected, an average reading value of the CAP sensor is used for determining. A subsequent entire process may be similar to a procedure of initial-state detection. It can be learned from the foregoing procedure that a policy is as follows. In the not-worn state, status determining is mainly performed by using the reading value of the CAP sensor, so as to reduce power consumption, when a status cannot be determined by using the reading value of the CAP sensor, an IR sensor is turned on and a reading value of the IR sensor is used for determining.

Figure 7:
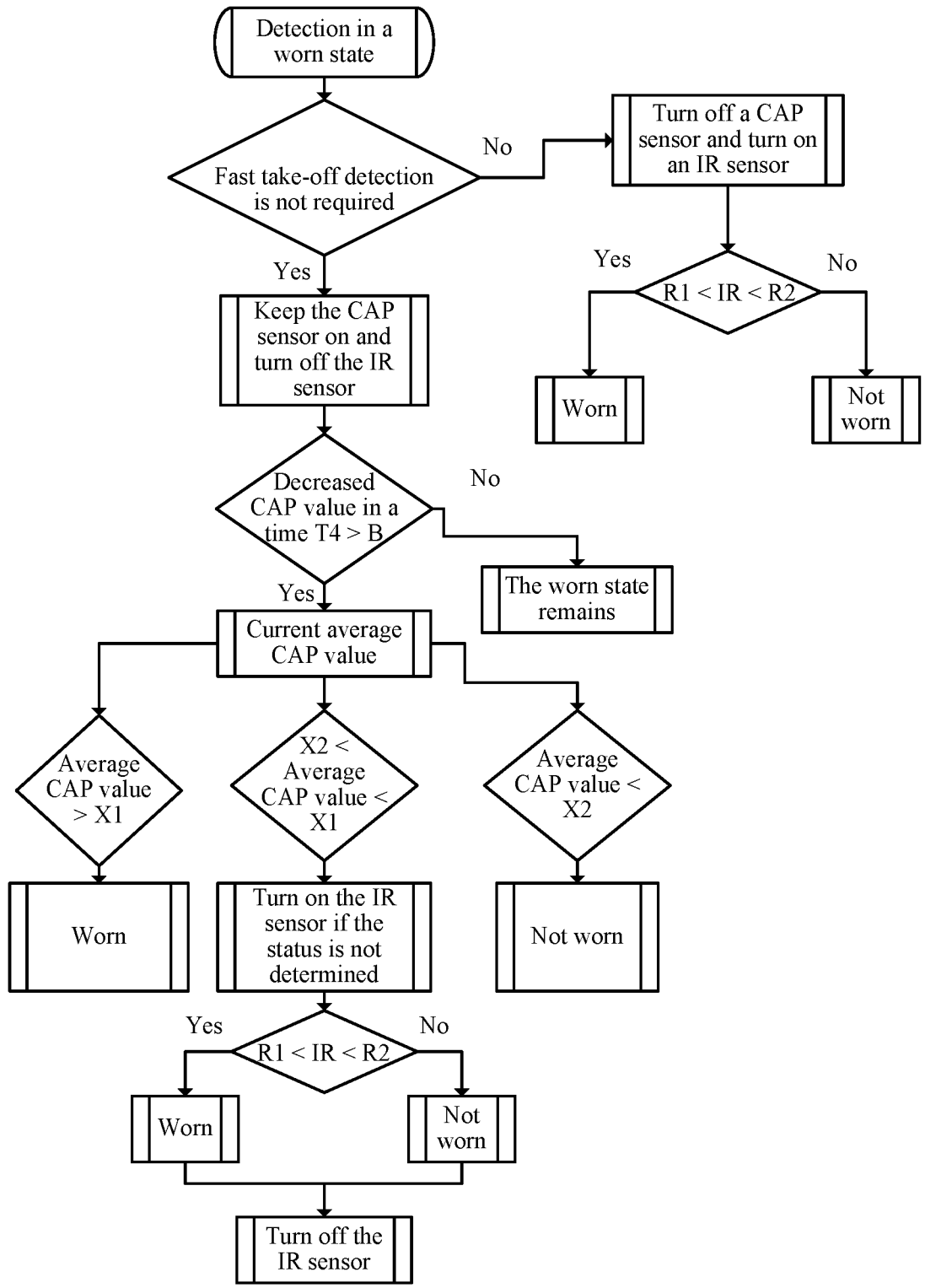
FIG. 7 is a schematic flowchart of detection in a worn state according to an embodiment of the present invention.

FIG. 7 is a schematic flowchart of detection in a worn state according to an embodiment of the present invention. It can be learned from a data collection example of a CAP sensor that stability of data of the CAP sensor is poorer than that of data of an IR sensor. When a reading value of the CAP sensor is used for determining in wearing detection, smoothing is required for a period of time before a reliable value is obtained. Therefore, in some scenarios requiring fast take-off action detection, using the reading value of the CAP sensor for determining cannot meet a requirement. In these scenarios, for example, when a watch is used for payment, fast take-off action detection is required, and a user needs to enter a password for payment after taking off the watch, so as to ensure payment security. Based on such consideration, detection in a worn state is further divided into two scenarios, including a scenario requiring fast take-off detection and a scenario not requiring fast take-off detection.

In the scenario not requiring fast take-off detection, detection by using the CAP sensor is still mainly used for determining. A take-off action may occur when the CAP sensor detects a falling edge. In this case, similar to the foregoing initial-state detection and/or detection in a not-worn state, a procedure of determining by using an average reading value of the CAP sensor and IR-sensor-assisted determining is started.

In the scenario requiring fast take-off detection, the CAP sensor is turned off, and a wearing detection result is output merely by using a reading value of the IR sensor.

Figure 8:
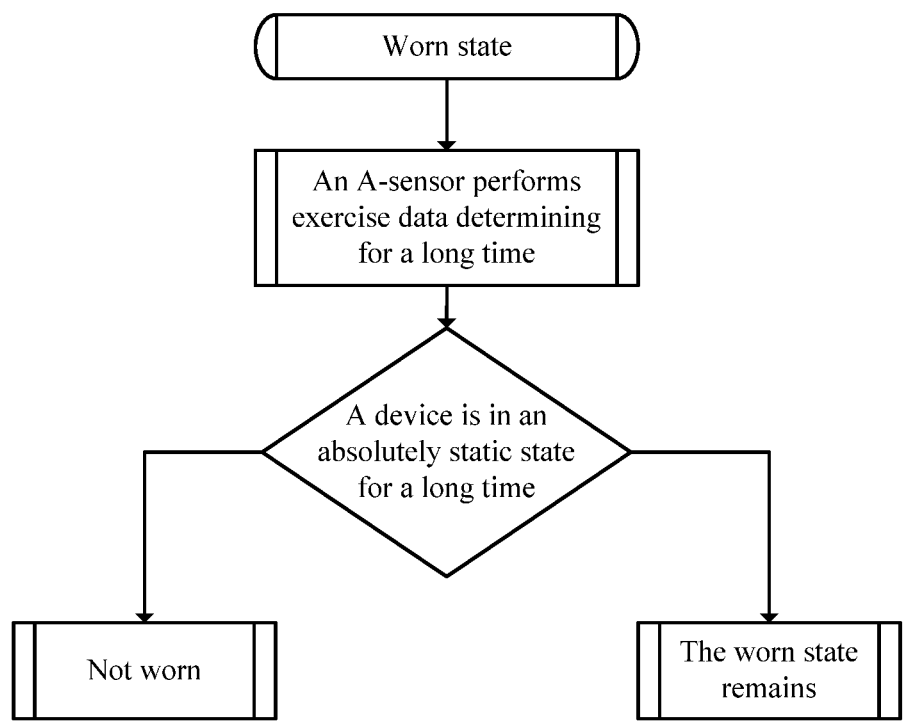
FIG. 8 is a schematic flowchart of an A-sensor-assisted correction method for wearing status detection according to an embodiment of the present invention.

FIG. 8 is a schematic flowchart of an A-sensor-assisted correction method for wearing status detection according to an embodiment of the present invention. When a user exercises wearing a device, an A-sensor may detect and output acceleration data of an exercise of the user in three directions of X, Y, and Z axes based on an exercise amplitude of the user. When the device is statically placed, data output in these three directions is noise data of the component, and the amplitude is at a relatively low level. If the acceleration data output by the device is at a noise level of the device for a long time, that the device is in a static state may be determined. In this case, if that the device is in a worn state is determined logically by using a CAP sensor and/or an IR sensor, the state is corrected by using the data of the A-sensor, so as to output a not-worn state. This improves wearing detection accuracy.

A measurement value of the acceleration sensor includes some noise itself. In a scenario in which the device is not worn and statically placed on a desktop and in a scenario in which the user wears the device but almost does not move, acceleration eigenvalues are similar in a short time, and therefore, a worn state and a not-worn state cannot be differentiated based on these values. However, in a relatively long time, for example, in two hours, it is difficult for the user to remain at a relatively low level of moving for such a long time. Therefore, if it is determined, by using the acceleration eigenvalues, that acceleration remains at a level equivalent to a noise level of the component itself for a long time, it may be considered that the device is not worn and in a static state.

In the present invention, a multi-sensor technology is combined for wearing detection, thereby improving wearing detection accuracy. In addition, a different detection solution is used based on a use scenario, thereby reducing power consumption for wearing detection. Using this technology for an intelligent wearable device improves user experience.

This technical solution is mainly used in scenarios in which the intelligent wearable device performs wearing detection. Such devices include wrist-wearable devices including a smart band, a smart watch, and the like, and another wearable device such as a smart necklace, provided that a main body of a worn device comes in good contact with a human body.

In the foregoing wearing detection procedure, data of a plurality of sensors is combined. Wearing detection is performed based on different application scenarios. The sensors may be, but not limited to, a CAP sensor, an IR sensor, and an A-sensor. For example, a heart rate detection sensor and/or a body temperature detection sensor may be added. When that the device is seemingly in a worn state and/or a not-worn state is determined, readings of the heart rate sensor and/or the body temperature detection sensor are used for state determining. Power consumption is relatively high when the heart rate sensor and the body temperature detection sensor are operating, and therefore, these sensors cannot remain in a steady-on state. Otherwise, a standby time and an operating time of the device are greatly affected. Therefore, when accurate identification cannot be implemented by using another sensor with low power consumption, these sensors are then turned on for state determining. This can improve detection accuracy while reducing power consumption.

In the embodiments of the present invention, the intelligent device may include one and/or a plurality of processors. When the intelligent device includes a plurality of processors, a wearing detection algorithm may be run on the MCU, or be run on another processor based on different hardware solutions, for example, on an application (AP) processor of a watch.

A person skilled in the art may be further aware that, in combination with the examples described in the embodiments disclosed in this specification, units and algorithm steps may be implemented by electronic hardware, computer software, or a combination thereof. To clearly describe the interchangeability between the hardware and the software, the foregoing has generally described compositions and steps of each example based on functions. Whether the functions are performed by hardware or software depends on particular applications and design constraint conditions of the technical solutions. A person skilled in the art may use different methods to implement the described functions for each particular application, but it should not be considered that the implementation goes beyond the scope of the present invention.

A person of ordinary skill in the art may understand that all or a part of the steps in each of the foregoing method of the embodiments may be implemented by a program instructing a processor. The foregoing program may be stored in a computer readable storage medium. The storage medium may be a non-transitory medium, such as a random-access memory, a read-only memory, a flash memory, a hard disk, a solid state drive, a magnetic tape, a floppy disk, an optical disc, or any combination thereof.

The foregoing descriptions are merely specific example implementations of the present invention, but are not intended to limit the protection scope of the present invention. Any variation and/or replacement readily figured out by a person skilled in the art within the technical scope disclosed in the present invention shall fall within the protection scope of the present invention. Therefore, the protection scope of the present invention shall be subject to the protection scope of the claims.

What is claimed is:

1. A method, comprising:
    obtaining a first measurement value of a first sensor of an intelligent device, the intelligent device further comprising a second sensor;
    when the first measurement value of the first sensor is greater than a first threshold, determining that the intelligent device is in a worn state;
    when the first measurement value of the first sensor is less than a second threshold, determining that the intelligent device is in a not-worn state, wherein the first threshold is greater than the second threshold; and
    when the first measurement value of the first sensor is greater than, or equal to, the second threshold, and less than, or equal to, the first threshold:
        turning on the second sensor;
        obtaining a second measurement value of the second sensor; and
        determining, according to the second measurement value of the second sensor, that the intelligent device is in the worn state or in the not-worn state.

2. The method according to claim 1, wherein the first sensor is a capacitive sensor, wherein the second sensor is an infrared sensor, and
    wherein the determining, according to the second measurement value of the second sensor, that the intelligent device is in the worn state or in the not-worn state comprises at least one of:
        when the second measurement value is greater than, or equal to, a third threshold, and less than, or equal to, a fourth threshold, determining that the intelligent device is in the worn state, wherein the third threshold is less than the fourth threshold; or
        when the second measurement value is greater than the fourth threshold, or when the second measurement value is less than the third threshold, determining that the intelligent device is in the not-worn state.

3. The method according to claim 1, wherein the first sensor is a capacitive sensor, wherein the second sensor is a heart rate detection sensor, and
    wherein the determining, according to the second measurement value of the second sensor, that the intelligent device is in the worn state or in the not-worn state comprises at least one of:
        when the second measurement value is greater than, or equal to, a fifth threshold, and less than, or equal to, a sixth threshold, determining that the intelligent device is in the worn state, wherein the fifth threshold is less than the sixth threshold; or
        when the second measurement value is greater than the sixth threshold, or when the second measurement value of the heart rate detection sensor is less than the fifth threshold, determining that the intelligent device is in the not-worn state.

4. The method according to claim 1, wherein the first sensor is a capacitive sensor, wherein the second sensor is a body temperature detection sensor, and
    wherein the determining, according the second measurement value of the second sensor, that the intelligent device is in the worn state or in the not-worn state comprises at least one:
        when the second measurement value is greater than, or equal to, a seventh threshold, and less than, or equal to, an eighth threshold, determining that the intelligent device is in the worn state, wherein the seventh threshold is less than the eighth threshold; or
        when the second measurement value is greater than the eighth threshold, or when the second measurement value of the body temperature detection sensor is less than the seventh threshold, determining that the intelligent device is in the not-worn state.

5. The method according to claim 1, wherein the first sensor is a capacitive sensor, and wherein the method further comprises:
    before the obtaining the first measurement value of the first sensor:
        determining a current status of the intelligent device, wherein the current status is one of a power-on initial state, the not-worn state, or the worn state;
        when determining that the current status is the not-worn state, determining that an increased value of the first measurement value in a first preset duration is greater than a ninth threshold; and
        when determining that the current status is the worn state, determining that a decreased value of the first measurement value in a second preset duration is greater than a tenth threshold.

6. The method according to claim 5, wherein the method further comprises:
    when determining that the current status is the worn state, determining, based on configuration information of an application enabled on the intelligent device, that fast take-off action detection is not required.

7. The method according to claim 1, wherein the intelligent device further comprises a third sensor, wherein the third sensor is an acceleration sensor, and
    wherein the method further comprises:
        obtaining a third measurement value of the acceleration sensor in a third preset duration; and when the third measurement value of the acceleration sensor in the third preset duration is less than an eleventh threshold, determining that the intelligent device is in the not- worn state.

8. The method according to claim 1, wherein the method further comprises:
after the determining, according to the second measurement value of the second sensor, that the intelligent device is in the worn state or in the not-worn state:
turning off the second sensor.

9. An intelligent device, comprising:
a first sensor;
a second sensor;
a processor; and
a non-transitory computer-readable storage medium storing a program to be executed by the processor, the program including instructions for:
obtaining a first measurement value of the first sensor;
when the first measurement value of the first sensor is greater than a first threshold, determining that the intelligent device is in a worn state;
when the first measurement value of the first sensor is less than a second threshold, determining that the intelligent device is in a not-worn state, wherein the first threshold is greater than the second threshold; and
when the first measurement value of the first sensor is greater than, or equal to, the second threshold, and less than, or equal to, the first threshold:
turning on the second sensor;
obtaining a second measurement value of the second sensor; and
determining, based on the second measurement value of the second sensor, that the intelligent device is in the worn state or in the not-worn state.

10. The intelligent device according to claim 9, wherein the first sensor is a capacitive sensor, wherein the second sensor is an infrared sensor, and
wherein the determining, based on the second measurement value of the second sensor, that the intelligent device is in the worn state or in the not-worn state comprises at least one of:
when the second measurement value is greater than, or equal to, a third threshold, and less than, or equal to, a fourth threshold, determining that the intelligent device is in the worn state, wherein the third threshold is less than the fourth threshold; or
when the second measurement value is greater than the fourth threshold, or when the second measurement value is less than the third threshold, determining that the intelligent device is in the not-worn state.

11. The intelligent device according to claim 9, wherein the first sensor is a capacitive sensor, wherein the second sensor is a heart rate detection sensor, and
wherein the determining, based on the second measurement value of the second sensor, that the intelligent device is in the worn state or in the not-worn state comprises at least one of:
when the second measurement value is greater than, or equal to, a fifth threshold, and less than, or equal to, a sixth threshold, determining that the intelligent device is in the worn state, wherein the fifth threshold is less than the sixth threshold; or
when the second measurement value is greater than the sixth threshold, or when the second measurement value of the heart rate detection sensor is less than the fifth threshold, determining that the intelligent device is in the not-worn state.

12. The intelligent device according to claim 9, wherein the first sensor is a capacitive sensor, wherein the second sensor is a body temperature detection sensor, and
wherein the determining, based on the second measurement value of the second sensor, that the intelligent device is in the worn state or in the not-worn state comprise at least one of:
when the second measurement value is greater than, or equal to, a seventh threshold, and less than, or equal to, an eighth threshold, determining that the intelligent device is in the worn state, wherein the seventh threshold is less than the eighth threshold; or
when the second measurement value is greater than the eighth threshold, or when the second measurement value is less than the seventh threshold, determining that the intelligent device is in the not-worn state.

13. The intelligent device according to claim 9, wherein the first sensor is a capacitive sensor, and wherein the program further includes instructions for:
before the obtaining the first measurement value of the first sensor:
determining a current status of the intelligent device, wherein the current status is one of a power-on initial state, the not-worn state, and the worn state;
when determining that the current status is the not-worn state, determining that an increased value of the first measurement value in a first preset duration is greater than a ninth threshold; and
when determining that the current status is the worn state, determining that a decreased value of the first measurement value in a second preset duration is greater than a tenth threshold.

14. The intelligent device according to claim 13, wherein the program further includes instructions for:
when determining that the current status is the worn state, determining, based on configuration information of an application enabled on the intelligent device, that fast take-off action detection is not required.

15. The intelligent device according to claim 9, wherein the intelligent device further comprises a third sensor, wherein the third sensor is an acceleration sensor, and
wherein the program further includes instructions for:
obtaining a third measurement value of the acceleration sensor in a third preset duration; and
when the third measurement value of the acceleration sensor in the third preset duration is less than an eleventh threshold, determining that the intelligent device is in the not- worn state.

16. The intelligent device according to claim 9, wherein the program further includes instructions for:
after the determining, based on the second measurement value of the second sensor, that the intelligent device is in the worn state or in the not-worn state:
turning off the second sensor.

17. A non-transitory computer readable storage medium storing a program, wherein the program comprises instructions, and when the instructions are executed by an intelligent device, the intelligent device performs a method, the method comprising:
obtaining a first measurement value of a first sensor of the intelligent device, the intelligent device further comprising a second sensor;
when the first measurement value of the first sensor is greater than a first threshold, determining that the intelligent device is in a worn state;

when the first measurement value of the first sensor is less than a second threshold, determining that the intelligent device is in a not-worn state, wherein the first threshold is greater than the second threshold, and when the first measurement value of the first sensor is greater than, or equal to, the second threshold, and less than, or equal to, the first threshold:
turning on the second sensor;
obtaining a second measurement value of the second sensor; and
determining, based on the second measurement value of the second sensor, that the intelligent device is in the worn state or in the not-worn state.

18. The non-transitory computer readable storage medium according to claim 17, wherein the first sensor is a capacitive sensor, wherein the second sensor is an infrared sensor, and
wherein the determining, based on the second measurement value of the second sensor, that the intelligent device is in the worn state or in the not-worn state comprises at least one of:
when the second measurement value is greater than, or equal to, a third threshold, and less than, or equal to, a fourth threshold, determining that the intelligent device is in the worn state, wherein the third threshold is less than the fourth threshold; or
when the second measurement value is greater than the fourth threshold, or when the second measurement value is less than the third threshold, determining that the intelligent device is in the not-worn state.

19. The non-transitory computer readable storage medium according to claim 17, wherein the first sensor is a capacitive sensor, wherein the second sensor is a heart rate detection sensor, and
wherein the determining, based on the second measurement value of the second sensor, that the intelligent device is in the worn state or in the not-worn state comprises at least one of:
when the second measurement value is greater than, or equal to, a fifth threshold, and less than, or equal to, a sixth threshold, determining that the intelligent device is in the worn state, wherein the fifth threshold is less than the sixth threshold; or
when the second measurement value of the heart rate detection sensor is greater than the sixth threshold, or when the second measurement value is less than the fifth threshold, determining that the intelligent device is in the not-worn state.

20. The non-transitory computer readable storage medium according to claim 17, wherein the first sensor is a capacitive sensor, wherein the second sensor is a body temperature detection sensor, and
wherein the determining, based on the second measurement value of the second sensor, that the intelligent device is in the worn state or in the not-worn state comprises at least one of:
when the second measurement value is greater than, or equal to, a seventh threshold, and less than, or equal to, an eighth threshold, determining that the intelligent device is in the worn state, wherein the seventh threshold is less than the eighth threshold; or
when the second measurement value is greater than the eighth threshold, or when the second measurement value is less than the seventh threshold, determining that the intelligent device is in the not-worn state.

* * * * *